(12) United States Patent
Ottma et al.

(10) Patent No.: US 10,492,906 B2
(45) Date of Patent: *Dec. 3, 2019

(54) CATHETER SYSTEM FOR IMPLANTATION OF PROSTHETIC HEART VALVES

(71) Applicant: JENAVALVE TECHNOLOGY, INC., Irvine, CA (US)

(72) Inventors: Rüdiger Ottma, Großschwabhausen (DE); Robert Moszner, Bad Klosterlausnitz (DE); Hans-Reiner Figulla, Jena (DE); Markus Ferrari, Jena (DE); Christoph Damm, Jena (DE)

(73) Assignee: JenaValve Technology, Inc., Irvine, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 15/700,366

(22) Filed: Sep. 11, 2017

(65) Prior Publication Data

US 2018/0021132 A1 Jan. 25, 2018

Related U.S. Application Data

(63) Continuation of application No. 15/464,891, filed on Mar. 21, 2017, now Pat. No. 9,788,945, which is a
(Continued)

(30) Foreign Application Priority Data

Jan. 20, 2005 (DE) ........................ 10 2005 003 632

(51) Int. Cl.
*A61F 2/24* (2006.01)
*A61F 2/95* (2013.01)

(52) U.S. Cl.
CPC .......... *A61F 2/2427* (2013.01); *A61F 2/2418* (2013.01); *A61F 2/2436* (2013.01); *A61F 2002/9517* (2013.01); *A61F 2240/008* (2013.01)

(58) Field of Classification Search
CPC ...... A61F 2/2427; A61F 2/243; A61F 2/2436; A61F 2/2439; A61F 2/95; A61F 2/962;
(Continued)

(56) References Cited

U.S. PATENT DOCUMENTS 4,922,905 A 5/1990 Strecker
5,002,566 A 3/1991 Carpentier et al.
(Continued)

FOREIGN PATENT DOCUMENTS

AU 2006308187 A1 5/2007
AU 2006310681 A1 5/2007
(Continued)

OTHER PUBLICATIONS

Aortenklappenbioprothese erfolgreich in der Entwicklung, May 16, 2003 (1 page).
(Continued)

*Primary Examiner* — Melanie R Tyson
(74) *Attorney, Agent, or Firm* — Bookoff McAndrews, PLLC

(57) ABSTRACT

A catheter is described for the transvascular implantation of prosthetic heart valves, e.g., including self-expanding anchorage supports, to reduce the risk to the patient during the implantation. Accordingly, a prosthetic heart valve with anchorage supports is temporarily housed in a folded form in a cartridge-type unit during the implantation. The cartridge-type unit can be fixed on the proximal end of a guide system, which includes a flexible region that can be guided through the aorta. Actuating elements run through the inte-
(Continued)

rior of the hollow guide system, permitting sections of the cartridge-type unit to be displaced radially about their longitudinal axis and/or laterally in a proximal direction, thus allowing individual sections of the anchorage support and the associated prosthetic heart valve to be sequentially released.

20 Claims, 6 Drawing Sheets

Related U.S. Application Data continuation of application No. 14/168,976, filed on Jan. 30, 2014, now Pat. No. 9,775,705, which is a continuation of application No. 11/795,590, filed as application No. PCT/DE2006/000056 on Jan. 12, 2006, now Pat. No. 8,679,174.

(58) Field of Classification Search
CPC ...... A61F 2002/9505; A61F 2002/9511; A61F 2002/9517; A61F 2002/9522; A61F 2002/9528; A61F 2002/9534; A61F 2002/011

See application file for complete search history.

(56) References Cited

U.S. PATENT DOCUMENTS

| | | | |
|---|---|---|---|
| 5,053,008 A | 10/1991 | Bajaj | |
| 5,061,277 A | 10/1991 | Carpentier et al. | |
| 5,094,661 A | 3/1992 | Levy et al. | |
| 5,104,407 A | 4/1992 | Lam et al. | |
| 5,197,979 A | 3/1993 | Quintero et al. | |
| 5,279,612 A | 1/1994 | Eberhardt | |
| 5,332,402 A | 7/1994 | Teitelbaum | |
| 5,336,258 A | 8/1994 | Quintero et al. | |
| 5,352,240 A | 10/1994 | Ross | |
| 5,368,608 A | 11/1994 | Levy et al. | |
| 5,411,552 A | 5/1995 | Andersen et al. | |
| 5,456,713 A | 10/1995 | Chuter | |
| 5,509,930 A | 4/1996 | Love | |
| 5,549,666 A | 8/1996 | Hata et al. | |
| 5,595,571 A | 1/1997 | Jaffe et al. | |
| 5,613,982 A | 3/1997 | Goldstein | |
| 5,632,778 A | 5/1997 | Goldstein | |
| 5,674,298 A | 10/1997 | Levy et al. | |
| 5,679,112 A | 10/1997 | Levy et al. | |
| 5,683,451 A | 11/1997 | Lenker et al. | |
| 5,697,972 A | 12/1997 | Kim et al. | |
| 5,713,953 A | 2/1998 | Vallana et al. | |
| 5,746,775 A | 5/1998 | Levy et al. | |
| 5,755,777 A | 5/1998 | Chuter | |
| 5,824,041 A | 10/1998 | Lenker et al. | |
| 5,824,080 A | 10/1998 | Lamuraglia | |
| 5,840,081 A | 11/1998 | Andersen et al. | |
| 5,841,382 A | 11/1998 | Walden et al. | |
| 5,843,181 A | 12/1998 | Jaffe et al. | |
| 5,855,601 A | 1/1999 | Bessler et al. | |
| 5,876,434 A | 3/1999 | Flomenblit et al. | |
| 5,880,242 A | 3/1999 | Hu et al. | |
| 5,885,238 A | 3/1999 | Stevens et al. | |
| 5,899,936 A | 5/1999 | Goldstein | |
| 5,928,281 A | 7/1999 | Huynh et al. | |
| 5,935,163 A | 8/1999 | Gabbay | |
| 5,104,407 B1 | 9/1999 | Lam et al. | |
| 6,001,126 A | 12/1999 | Nguyen-Thien-Nhon | |
| 5,061,277 B1 | 2/2000 | Carpentier et al. | |
| 6,077,297 A | 6/2000 | Robinson et al. | |
| 6,093,530 A | 7/2000 | McIlroy et al. | |
| 6,102,944 A | 8/2000 | Huynh et al. | |
| 6,117,169 A | 9/2000 | Moe | |
| 6,126,685 A | 10/2000 | Lenker et al. | |
| 6,168,614 B1 | 1/2001 | Andersen et al. | |
| 6,177,514 B1 | 1/2001 | Pathak et al. | |
| 6,183,481 B1 | 2/2001 | Lee et al. | |
| 6,200,336 B1 | 3/2001 | Pavcnik et al. | |
| 6,214,055 B1 | 4/2001 | Simionescu et al. | |
| 6,231,602 B1 | 5/2001 | Carpentier et al. | |
| 6,254,564 B1 | 7/2001 | Wilk et al. | |
| 6,254,636 B1 | 7/2001 | Peredo | |
| 6,273,876 B1 | 8/2001 | Klima et al. | |
| 6,283,995 B1 | 9/2001 | Moe et al. | |
| 6,287,338 B1 | 9/2001 | Sarnowski et al. | |
| 6,338,740 B1 | 1/2002 | Carpentier | |
| 6,342,070 B1 | 1/2002 | Nguyen-Thien-Nhon | |
| 6,344,044 B1 | 2/2002 | Fulkerson et al. | |
| 6,350,278 B1 | 2/2002 | Lenker et al. | |
| 6,379,740 B1 | 4/2002 | Rinaldi et al. | |
| 6,391,538 B1 | 5/2002 | Vyavahare et al. | |
| 6,425,916 B1 | 7/2002 | Garrison et al. | |
| 6,454,799 B1 | 9/2002 | Schreck | |
| 6,471,723 B1 | 10/2002 | Ashworth et al. | |
| 6,478,819 B2 | 11/2002 | Moe | |
| 6,508,833 B2 | 1/2003 | Pavcnik et al. | |
| 6,509,145 B1 | 1/2003 | Torrianni | |
| 6,521,179 B1 | 2/2003 | Girardot et al. | |
| 6,540,782 B1 | 4/2003 | Snyders | |
| 6,558,417 B2 | 5/2003 | Peredo | |
| 6,558,418 B2 | 5/2003 | Carpentier et al. | |
| 6,572,642 B2 | 6/2003 | Rinaldi et al. | |
| 6,582,462 B1 | 6/2003 | Andersen et al. | |
| 6,585,766 B1 | 7/2003 | Huynh et al. | |
| 6,613,086 B1 | 9/2003 | Moe et al. | |
| 6,682,559 B2 | 1/2004 | Myers et al. | |
| 6,730,118 B2 | 5/2004 | Spenser et al. | |
| 6,736,845 B2 | 5/2004 | Marquez et al. | |
| 6,767,362 B2 | 7/2004 | Schreck | |
| 6,790,230 B2 | 9/2004 | Beyersdorf et al. | |
| 6,808,529 B2 | 10/2004 | Fulkerson | |
| 6,821,211 B2 | 11/2004 | Otten et al. | |
| 6,821,297 B2 | 11/2004 | Snyders | |
| 6,824,970 B2 | 11/2004 | Vyavahare et al. | |
| 6,830,584 B1 | 12/2004 | Seguin | |
| 6,861,211 B2 | 3/2005 | Levy et al. | |
| 6,872,226 B2 | 3/2005 | Cali et al. | |
| 6,881,199 B2 | 4/2005 | Wilk et al. | |
| 6,893,460 B2 | 5/2005 | Spenser et al. | |
| 6,908,481 B2 | 6/2005 | Cribier | |
| 6,911,043 B2 | 6/2005 | Myers et al. | |
| 6,945,997 B2 | 9/2005 | Huynh et al. | |
| 6,974,474 B2 | 12/2005 | Pavcnik et al. | |
| 7,014,655 B2 | 3/2006 | Barbarash et al. | |
| 7,018,406 B2 | 3/2006 | Seguin et al. | |
| 7,037,333 B2 | 5/2006 | Myers et al. | |
| 7,050,276 B2 | 5/2006 | Nishiyama | |
| 7,078,163 B2 | 7/2006 | Torrianni | |
| 7,081,132 B2 | 7/2006 | Cook et al. | |
| 7,137,184 B2 | 11/2006 | Schreck | |
| 7,141,064 B2 | 11/2006 | Scott et al. | |
| 7,163,556 B2 | 1/2007 | Xie et al. | |
| 7,189,259 B2 | 3/2007 | Simionescu et al. | |
| 7,198,646 B2 | 4/2007 | Figulla et al. | |
| 7,201,772 B2 | 4/2007 | Schwammenthal et al. | |
| 7,238,200 B2 | 7/2007 | Lee et al. | |
| 7,252,682 B2 | 8/2007 | Seguin | |
| 7,318,278 B2 | 1/2008 | Zhang et al. | |
| 7,318,998 B2 | 1/2008 | Goldstein et al. | |
| 7,322,932 B2 | 1/2008 | Xie et al. | |
| 7,329,278 B2 | 2/2008 | Seguin et al. | |
| 7,381,218 B2 | 6/2008 | Schreck | |
| 7,393,360 B2 | 7/2008 | Spenser et al. | |
| 7,399,315 B2 | 7/2008 | Iobbi | |
| 7,452,371 B2 | 11/2008 | Pavcnik et al. | |
| 7,473,275 B2 | 1/2009 | Marquez | |
| 8,679,174 B2 * | 3/2014 | Ottma ................... | A61F 2/2418 623/2.11 |
| 9,788,945 B2 * | 10/2017 | Ottma ................... | A61F 2/2418 |
| 2001/0011187 A1 | 8/2001 | Pavcnik et al. | |
| 2001/0039450 A1 | 11/2001 | Pavcnik et al. | |
| 2002/0032481 A1 | 3/2002 | Gabbay | |
| 2002/0055775 A1 | 5/2002 | Carpentier et al. | |
| 2002/0120322 A1 | 8/2002 | Thompson et al. | |

(56) References Cited

U.S. PATENT DOCUMENTS

| | | |
|---|---|---|
| 2002/0123790 A1 | 9/2002 | White et al. |
| 2002/0133226 A1 | 9/2002 | Marquez et al. |
| 2002/0193871 A1 | 12/2002 | Beyersdorf et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0044350 A1 | 3/2004 | Martin et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0093063 A1* | 5/2004 | Wright ............... A61F 2/95 623/1.12 |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0243143 A1 | 12/2004 | Corcoran et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137691 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0154355 A1 | 6/2008 | Benichou et al. |
| 2008/0255660 A1 | 6/2008 | Guyenot et al. |
| 2008/0200977 A1 | 8/2008 | Paul et al. |
| 2008/0215143 A1 | 9/2008 | Seguin |
| 2008/0255661 A1 | 10/2008 | Straubinger et al. |
| 2008/0262590 A1 | 10/2008 | Murray |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0005863 A1 | 1/2009 | Goetz et al. |
| 2009/0222076 A1 | 9/2009 | Figulla et al. |
| 2010/0249915 A1 | 9/2010 | Zhang |
| 2010/0249916 A1 | 9/2010 | Zhang |
| 2010/0249917 A1 | 9/2010 | Zhang |

(56) References Cited

U.S. PATENT DOCUMENTS

2010/0249918 A1 9/2010 Zhang
2010/0286768 A1 11/2010 Alkhatib

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 10121210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| EP | 0084395 A1 | 7/1983 |
| EP | 0402036 B1 | 12/1990 |
| EP | 0402176 B1 | 12/1990 |
| EP | 0411118 A1 | 2/1991 |
| EP | 0458877 B1 | 4/1991 |
| EP | 0515324 A1 | 11/1992 |
| EP | 0547135 B1 | 6/1993 |
| EP | 0657147 A2 | 6/1995 |
| EP | 0871414 | 9/1995 |
| EP | 0 592 410 B1 | 11/1995 |
| EP | 0786970 A1 | 5/1996 |
| EP | 0729364 B1 | 9/1996 |
| EP | 0756498 B1 | 5/1997 |
| EP | 0778775 B1 | 6/1997 |
| EP | 0888142 | 9/1997 |
| EP | 0928615 A1 | 7/1999 |
| EP | 1051204 | 7/1999 |
| EP | 1089676 | 12/1999 |
| EP | 0986348 B1 | 3/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 253 875 B1 | 4/2005 |
| EP | 1 251 803 B1 | 6/2005 |
| EP | 1469797 B1 | 11/2005 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2002-525168 A | 8/2002 |
| JP | 2003-523262 | 8/2003 |
| JP | 2003-524504 | 8/2003 |
| JP | 2004-283461 A | 10/2004 |
| JP | 2005-118585 | 5/2005 |
| JP | 2007-296375 | 11/2007 |
| JP | 2008-539305 | 11/2008 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO 98/43556 | 10/1998 |
| WO | WO-98/46165 | 10/1998 |
| WO | WO-99/37337 | 7/1999 |
| WO | WO-99/53987 A1 | 10/1999 |
| WO | WO-99/66863 | 12/1999 |
| WO | WO 2000/02503 A1 | 1/2000 |
| WO | WO 00/15148 | 3/2000 |
| WO | WO 00/18330 | 4/2000 |
| WO | WO-00/18445 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 2001/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A2 | 7/2005 |
| WO | WO-2005/072654 A1 | 8/2005 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A2 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |

(56) References Cited

FOREIGN PATENT DOCUMENTS

| WO | WO 2007/098232 A2 | 8/2007 |
|---|---|---|
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |

OTHER PUBLICATIONS

English translation of Aortenklappenbioprothese erfolgreich in der Entwicklung (2 pages).

Screen shots from http://www.fraunhofer.de/presse/filme/2006/index.jsp, 2006 (2 pages).

Liang, Ma, et al., "Double-crowned valved stents for off-pump mitral valve replacement," *Eur. J. Cardio-Thoracic Surgery*, vol. 28, pp. 194-198 (2005) (5 pages).

Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).

English translation of DE 19546692 A1 (3 pages).

English translation of EP 1469797 B1 (15 pages).

File history for German Patent DE 195 46 692 filed Dec. 14, 1995 and patented Jul. 11, 2002 (111 pages).

Ferrari, M. et al., "Transarterial Aortic Valve Replacement with a Self Expanding Stent in Pigs," Heart, vol. 90, pp. 1326-1331, (2004).

English abstract for DE 19857887 A1 (1 page).

English abstract for DE 10335948 B3 (1 page).

English abstract for DE 10034105 C1 (2 pages).

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

Ferrari, "Entwicklung eines Verfahrens zum transvaskulären Aortenklappenersatz," Habilitationsschrift, Medizinische Fakultät der Friedrich-Schiller-Universität Jena, pp. 49-52, dated Sep. 2003.

Ferrari, "Entwicklung eines Verfahrens zum transvaskulären Aortenklappenersatz," Habilitationsschrift, Medizinische Fakultät der Friedrich-Schiller-Universität Jena, pp. 1-159, dated Sep. 2003.

German National Library, bibliographic information for Ferrari, M., "Entwicklung eines Verfahrens zum transvaskulären Aortenklappenersatz," available at https://www.deutsche-digitale-bibliothek.de/item/U2RQV45RMES4YP6AHEPGN4QPJWAMGROI.

\* cited by examiner

CATHETER SYSTEM FOR IMPLANTATION OF PROSTHETIC HEART VALVES

This application is a continuation of U.S. application Ser. No. 15/464,891, filed on Mar. 21, 2017, which is a continuation of U.S. application Ser. No. 14/168,976, filed on Jan. 30, 2014, which is a continuation of U.S. application Ser. No. 11/795,590, filed on Jun. 5, 2008, now U.S. Pat. No. 8,679,174, which is the national stage entry under 35 U.S.C. § 371 of PCT/DE2006/000056, filed on Jan. 12, 2006, which claims priority to German Application No. 10 2005 003 632.5, filed on Jan. 20, 2005, each of which is incorporated by reference herein in its entirety.

The invention relates to catheters for the transvascular implantation of prosthetic heart valves with self-expanding anchoring systems, by means of which prosthetic heart valves can be implanted with minimal invasion.

It is becoming more frequently necessary for an increasing number of patients to have prosthetic heart valves implanted, for which purpose both artificial and biological implants are used for heart valve prostheses.

In the past, such operations have been conducted in such a way that it as necessary to use a heart-lung-machine on the anaesthetised patient. This therefore makes it a cost-intensive surgical intervention, which subjects the respective patients to a high degree of psychological and physical stress. The aim is to keep the lethality risk below 3%. As the age of the respective patients increases and impairment of the respective heart valves becomes more advanced, a situation is reached in which patients in need of actual treatment become inoperable. Since surgical valve replacement is not possible for these patients, they suffer from a reduce quality of life and have a considerably reduced life expectancy. Intervention would pose an extremely high risk.

These same issues also apply to operations whereby prosthetic heart valves with anchoring systems are implanted by means of so-called balloon catheters.

In a procedure of this type, incorrect positioning can occur, which can have considerable consequences for the patient, possibly leading to the death of the respective patient.

In recent times, therefore, attempts have been made to implant heart valve prostheses by means of intervention methods involving minimal invasion, whereby such prostheses are fed together with an anchoring support via the aorta of a patient and through the aorta to the heart. On reaching the implantation site at the heart, self-expansion of such anchoring supports with a heart valve prosthesis attached to them is initiated, the intended result being a reliable anchoring and exact positioning of the heart valve prosthesis. Such anchoring supports have tended to be made from shape memory alloys, such as "Nitinol" for example, and the alloy is selected so that its transition temperature is around 37° C., and self-expansion can be initiated on reaching the transition temperature.

As a result of such expansion, the anchoring support opens up so that it is able to lie against the aorta wall, where it can be securely fixed by means of additional barb elements if necessary. The heart valve prosthesis is folded open simultaneously, so that it is able to assume its function.

An anchoring support of this type incorporating a heart valve prosthesis is described in patent specification WO 2004/019825 A1, for example.

Support hoops are provided at the proximal end of such an anchoring support, which can be introduced into the pockets of a patient's heart valve, thereby enabling the anchoring support to be very accurately positioned by means of these support hoops during a surgical intervention. What are referred to as commissural hoops are provided on this anchoring support in addition, which, together with the support hoops, clamp parts of a patient's old heart valve once the anchoring support has unfolded so that the anchoring support can be reliably positioned and secured as a result of this clamping effect.

The support and commissural hoops of this known anchoring support should therefore be disposed and dimensioned so that they permit a sequential self-expansion. This means that the anchoring support is accommodated inside a cartridge for the implantation procedure. It is then fed by means of a catheter through the aorta as far as the diseased heart. On reaching the implantation site, the cartridge is manipulated so that the support hoops are released to allow them to self-expand. The cartridge is then moved and oriented together with the anchoring support so that the support hoops are introduced into the pockets of the heart valve of the respective patient. This enables exact positioning to be achieved.

The respective, cartridge is then further manipulated, so that the commissural hoops are also released and able to self-expand. As this happens, the old heart valve is clamped between the support and commissural hoops and the heart valve prosthesis is opened up into its unfolded functional position.

After implanting the anchoring support incorporating the heart valve prosthesis, the catheter can then be removed from the patient's body together with the cartridge through the aorta.

Although the support hoops provided on the anchoring support can result in significantly easier and better positioning of the heart valve prosthesis to be implanted in the manner described above, there is a possibility of incorrect implantation and the heart valve prosthesis may not be capable of functioning or may be so to only an unsatisfactory degree. In certain situations, it is then no longer possible to remove a non-functioning or unsatisfactorily functioning heart valve prosthesis and it poses an increased risk of mortality for the respective patient in some cases.

The bend in the aorta in the human body during introduction through the aorta poses another problem during such surgical interventions. As the cartridge and the respective catheter are moved during this procedure, a change of direction of approximately 180° with a relatively small radius of about 50 mm has to be negotiated without causing damage to the vessel wall.

Accordingly, the objective of the invention is to reduce risk to the patient during implantation of prosthetic heart valves.

This objective is achieved by the invention on the basis of a catheter incorporating the characterising features defined in claim 1. Advantageous embodiments and designs of the invention may be obtained on the basis of the characterising features defined in the dependent claims.

In a preferred embodiment, a catheter proposed by the invention may be used in conjunction with a heart valve prosthesis with a self-expanding anchoring support of the type known from patent specification WO 2004/019825 and the disclosed contents are included herein by way of reference.

This being the case, the anchoring support with the heart valve prosthesis attached to it can be temporarily accommodated inside a cartridge unit in a collapsed state during the implantation.

A cartridge unit prepared in this manner can be releasably attached to the proximal end of a guide system. The cartridge unit and guide system are minimised in term of their external diameter to the degree that they can be fed through an aorta of a patient to be operated on without any difficulty, and to this end, the total free cross-section available inside the aorta should not be completely filled.

The guide system used is sufficiently long in terms of its length for the cartridge unit to be fed with the guide system by introducing it into the groin of a patient, through the aorta as far as the patient's heart.

A flexible, bendable region is provided on the guide system, by means of which a bending radius and bending angle can be achieved that will follow and make allowance for the bend in the patient's aorta.

Elements for operating the cartridge unit are fed by means of the guide system, which has a hollow interior. These operating elements enable parts of the cartridge unit to be manipulated and moved in a specific way. For example, a radial or also lateral movement of parts of the cartridge unit can be effected by means of the operating elements. Moving parts of the cartridge unit in this specific way enables parts of the anchoring support to be released in sequence so that implantation and anchoring can take place in the manner described in WO 2004/019825.

For example, support hoops of an anchoring support can be released by a rotation or by a lateral movement in the proximal or distal direction of a part of the cartridge unit, but other parts, such as the commissural hoops for example, continue to be retained inside the cartridge unit in the collapsed state, which can subsequently be released with a view to expansion by moving another part of the cartridge unit accordingly or by continuing the movement of the same part of the cartridge unit which previously still enabled the support hoops to be retained inside the cartridge unit in the collapsed state.

The heart valve prosthesis, which is attached to the anchoring support by stitching for example, opens simultaneously as the respective hoops of the anchoring support, to which the heart valve prosthesis is attached, expand.

In a preferred embodiment, in addition to the operating elements for parts of the cartridge unit, other operating elements are fed through the internally hollow guide system, which act on the bendable region in order to influence its curvature in a specific manner.

Due in particular to traction forces triggered via the operating elements, a specific curvature of the bendable region can be achieved during the implantation on penetrating the bend of the aorta. Tension cables or tension wires may be used as the operating elements, which are run through the internally hollow guide system as far as the proximal edge of the bendable region, where they are secured on the guide system, in which case the attacking points of the force of two such operating elements should be disposed diametrically opposite one another and in addition-should be disposed at 90° with respect to the bending axis about which the bendable region is required to curve.

For example, the curvature of the bendable region can be influenced in a specific way by applying a traction force via one of the operating elements as the guide system is pushed through the bend in the aorta by means of the bendable region and pulled out of it once the implantation has been completed.

The bendable region of a guide system may be provided in the form of a link chain, in which the individual links are connected to one another by individual joints. This being the case, the individual joints positively engage in respective adjacent links. They are designed so that a curvature of more than 180° can be maintained in the bending region, with a bending radius which guarantees that at least the radius of the bend in the aorta can be achieved.

The individual joints on the individual links of a link chain should also be disposed diametrically opposite one another in pairs on the individual links and parallel with the rotation axis of the bendable region.

The guide system used with a catheter proposed by the invention should advantageously also be designed so that a liquid coolant or a pharmaceutical preparation can be circulated through the internally hollow guide system as far as the cartridge unit. With the aid of such a liquid coolant, for example a salt solution, the anchoring support can be kept below the transition temperature of the shape memory alloy. This also prevents body fluids from being able to penetrate the interior of the guide system and a liquid pressure should therefore be maintained which lends a sufficiently high resistance to penetration by body fluid or other elements contained in body fluid.

Introducing liquid coolant in an appropriate manner can also prevent gas, for example air, from getting into the aorta and the blood.

To this end, the entire guide system should be as liquid-proof as possible. Accordingly, a flexible, bendable region provided in the form of a link chain in this instance may be sealed from the outside by means of a plastic hose to render it liquid-proof.

The parts of the cartridge unit which can be moved in a specific way in order to release hoops of the anchoring support are preferably provided in the form of sleeve-shaped elements, the internal and external diameters of which are adapted to one another so that they can engage in one another telescopically, and at least two of the sleeve-shaped elements have mutually adapted internal and external diameters such that a collapsed anchoring support with heart valve prosthesis can be accommodated between them and retained in the collapsed state.

When introducing the catheter, the cartridge unit should be completely closed as far as possible and to facilitate introduction through the aorta should have a tip at its proximal end, which is in turn preferably made from a flexible material, for example silicone.

When the cartridge unit reaches the respective patient's heart, the appropriate manipulation can then be performed, in other words parts/sleeve-shaped elements of the cartridge unit moved, so that the different hoops of the anchoring support are sequentially released and the heart valve prosthesis secured to them simultaneously opened up.

As this happens, however, the anchoring support is still securely retained on the cartridge unit. To this end, anchoring elements are provided on one sleeve-shaped element of the cartridge unit, disposed at the distal end, for example at a point where eyes are provided on the anchoring support. In this position, these anchoring elements together with the distal part of the anchoring support are also covered by a sleeve-shaped element of the cartridge unit, so that the distal part of the anchoring element is still retained in the collapsed state.

In this position, it is possible to check the function of the heart valve prosthesis, which has already unfolded. Once it is evident that the heart valve prosthesis is functioning, a further manipulation may be effected by moving the sleeve element that was previously covering the anchoring element with the distal part of the anchoring support accordingly, which causes the distal part of the anchoring support to be fully released as well so that it can then fully unfold.

If, on checking, it is found that the implanted heart valve prosthesis is not fulfilling its function or is so but not satisfactorily, it is advantageously possible to move the anchoring support together with the heart valve prosthesis back into the cartridge unit by moving the parts/sleeve-shaped elements in the opposite direction accordingly and removing all the parts, in other words the entire catheter, from the patient's body again, thereby significantly reducing the risk of the operation, after which a further attempt at implantation can be made on the same patient.

In one advantageous embodiment of the catheter proposed by the invention, a guide wire can also be run through the entire catheter. Such guide wires are already used for operations of this type and they are fed through the patient's aorta to a point behind the heart before introducing the catheter. The catheter can then be placed over the cartridge unit and guide system and into the guide wire and pushed in along it into the aorta as far as the patient's heart.

In order to monitor the process of introducing the catheter and also manipulation of the bendable region, in particular at the bend of the aorta, it is of advantage to provide marker elements on the guide system and/or the cartridge unit, made from a material which absorbs X-radiation, so that the respective position can be pinpointed on an X-ray image during the operation.

A screen filter may also be used with the catheter proposed by the invention, by means of which particles can be prevented from penetrating the respective patient's blood circulation system. Such a screen filter may be attached to the guide system so that it completely surrounds it in the radial direction. In this respect, it should be elastically biased so that it lies against the vessel wall of the aorta, thereby guaranteeing a closure that is impermeable to particles.

Furthermore, the catheter proposed by the invention may additionally be provided with a conventional balloon disposed in the interior of the guide system or cartridge unit and carried with it there or alternatively it can be fed through the interior of the guide system as far as the anchoring support to be expanded. Using such a balloon, the volume of which can be increased by means of a fluid at increased pressure, will further assist expansion of the anchoring support.

The operating elements described above, which may be fed through the interior of the guide system and provided in the form of traction and compression means, may advantageously be manipulated from a manipulating part. The manipulating part may be designed as a handle, by means of which the movement for introducing the catheter can then be effected by the respective surgeon.

Other control elements are also provided on such a manipulating part, by means of which the respective movement of the operating elements can be initiated. This being the case, it should be possible to effect the corresponding movement in as measured a manner as possible, for example with appropriate translation ratios, and it should be possible to restrict the respective movement by end stops or catch positions at least. This enables specific maximum distances or angles to be preserved, for which allowance can be made in achieving the sequential expansion of the anchoring support or the specific way in which the curvature of the bendable region is influenced. In this respect, it should be possible to adjust the end stops or individual catches as finely as possible.

All the parts of a catheter proposed by the invention but at least those which come into direct contact with the respective patient and are also introduced into the aorta should be made from bio-compatible materials which are compatible with the respective organism. It should also be possible to sterilise them, in which case it should be possible to use one of the standard sterilisation processes.

The invention will be explained in more detail on the basis of examples.

Of the drawings:

FIGS. 1 to 4 are intended to illustrate and provide a clearer understanding of an example of a catheter proposed by the invention. The individual diagrams illustrate different phases which take place during implantation of an anchoring support 10 incorporating a heart valve prosthesis.

Figure 1:
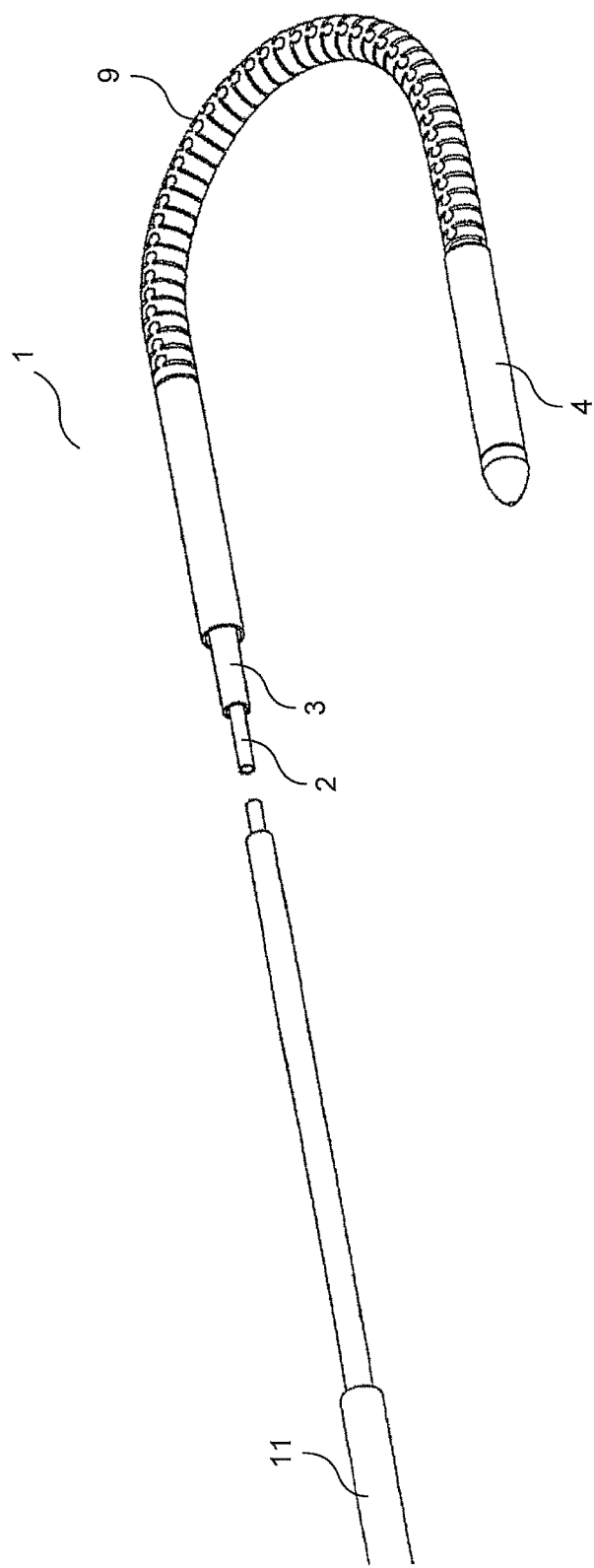
FIGS. 1 to 4 are schematic diagrams illustrating an example of a catheter proposed by the invention during different possible phases of an implantation procedure.

The example of a catheter proposed by the invention illustrated in FIG. 1 is shown with the cartridge unit 4, which is still completely closed, containing an anchoring support 10 incorporating a heart valve prosthesis in the non-expanded state and thus collapsed, so that it can be fed by means of the internally hollow guide system 1 through an appropriate access into the aorta and through it to the respective implantation site on the patient's heart.

Proximally disposed on the cartridge unit 4 is a flexible tip made from silicone, which facilitates the introduction procedure and reduces the risk of damage.

Part 5 of the cartridge unit is releasably connected to the other parts of the guide system 1, for example by means of a screw connection.

Adjoining the cartridge unit 4 is a bendable region 9, which is designed and dimensioned so that it is guaranteed to be able to move through the bend of a patient's aorta without causing problems.

Possible designs of such a bendable region 9 will be explained below.

Other parts of the internally hollow guide system 1 are also illustrated and FIGS. 1 to 4 show two operating elements 2 and 3 running through the guide system 1 as far as the cartridge unit 4, and in this instance the operating element 2 likewise runs through the internally hollow operating element 3 as far as the cartridge unit 4.

The operating elements 2 and 3 in this instance are provided in the form of lengths of compression spring, which are preferably reinforced by means of tension wire. Such tension wires make the catheter safer as it is being removed from the patient's body once the operation is complete.

Other parts 11 of the guide system 1 are illustrated on the left-hand side, which may be provided in the form of more or fewer sleeve-shaped parts, although these must be secured so that they are sufficiently pressure- and tension-resistant to withstand introduction into the aorta and extraction from the aorta again. Appropriately stiff plastic hoses may be used for this purpose, for example PTFE hoses or hoses with a PTFE base, because they are sufficiently compatible with the organism and can also be sterilised.

Figure 2:
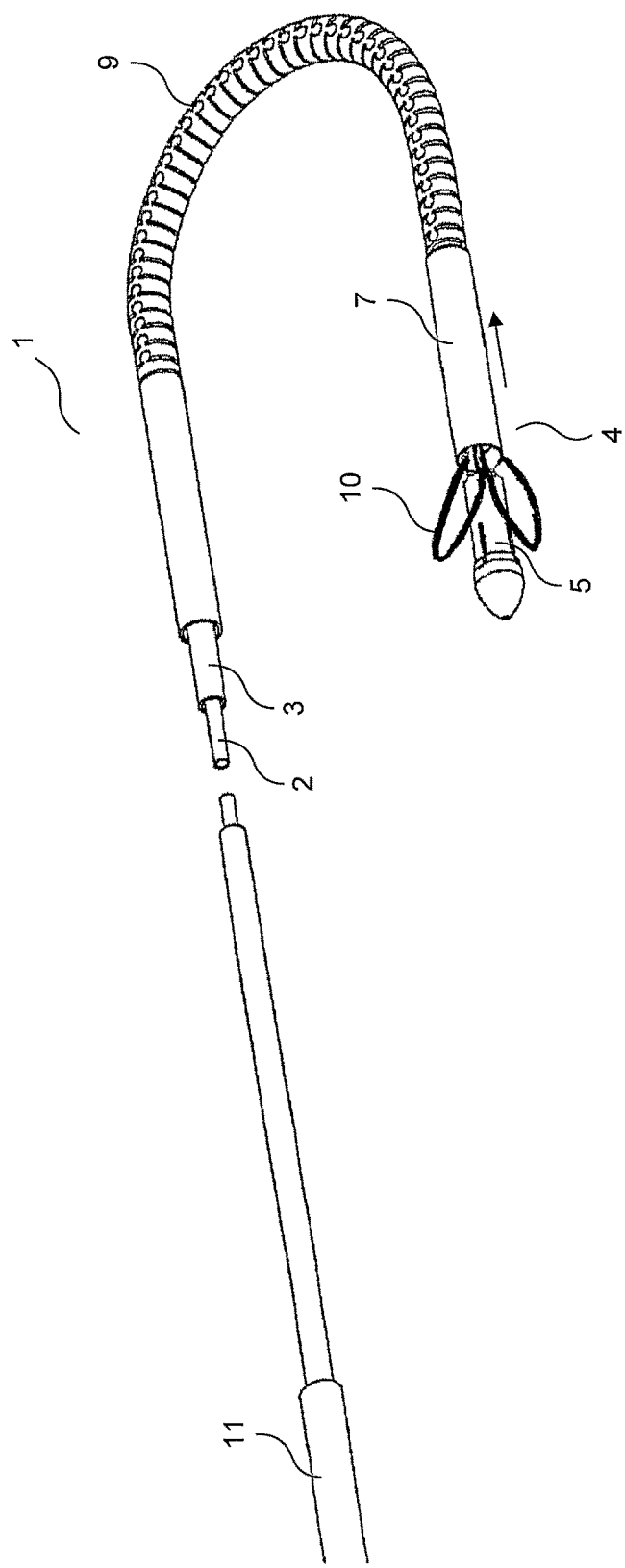

FIG. 2 illustrates the procedure which takes place during a first stage of the operation on reaching the implantation site on the respective patient's heart. The part/sleeve-shaped element 7 of the cartridge unit 4 can be pulled back in the distal direction by a distal movement of one of the operating elements 2 and/or 3 so that some hoops of the anchoring support 10, for example and preferably the support hoops provided on the known-heart valve prosthesis disclosed in WO 2004/019825 A1, expand and are biased radially outwards.

The entire catheter with the guide system 1 and the cartridge unit 4 can therefore be pushed proximally and these hoops (support hoops) introduced into the pockets of the patient's old heart valve. When the surgeon feels a perceptible resistance, the process of introducing the support hoops of the anchoring support 10 into the pockets of the old heart valve is complete.

The part/sleeve-shaped element 5 of the cartridge unit 4 can then be moved proximally forwards, so that other hoops of the anchoring support can then also be released so that they can self-expand and open up the heart valve prosthesis.

Figure 3:
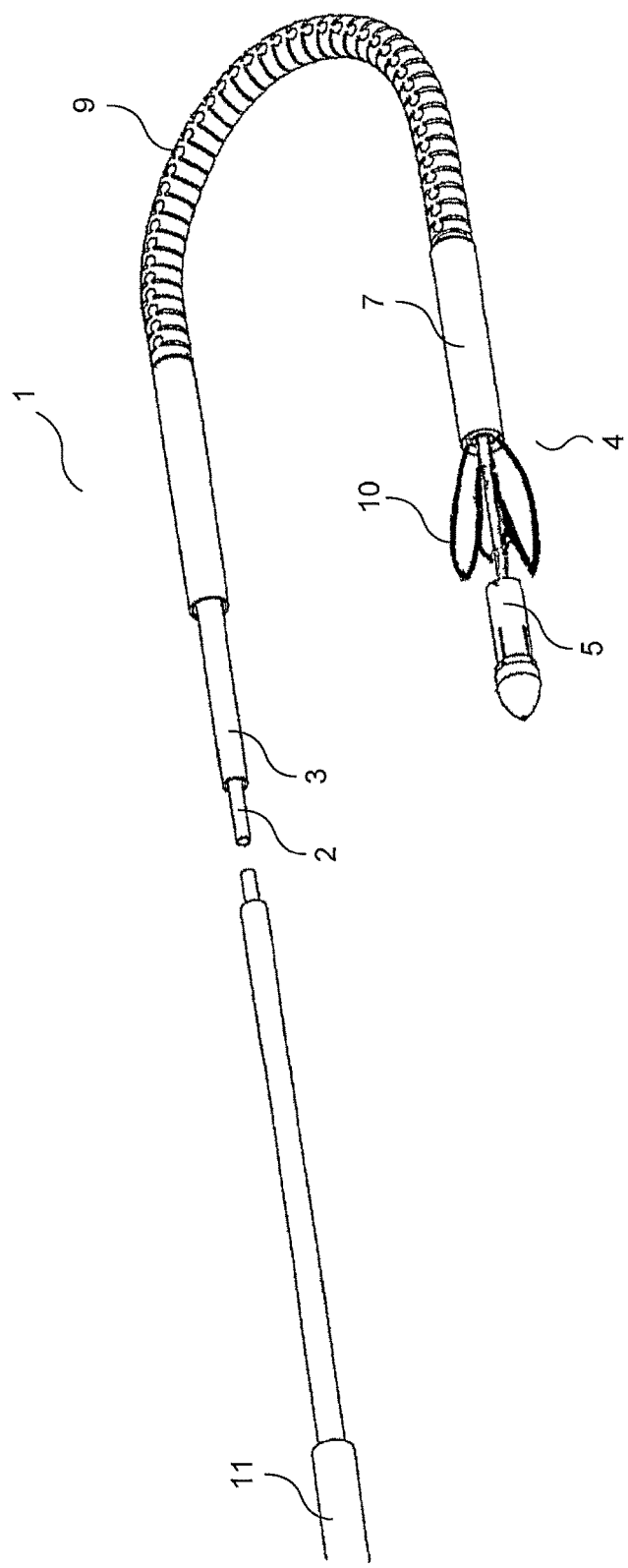

A preliminary stage of this is illustrated in FIG. 3, where a heart valve prosthesis has not yet been fully unfolded and the anchoring support 10 can also not yet be fully anchored.

As also illustrated in FIG. 3, a distal part of the anchoring support 10 is still accommodated inside the cartridge unit 4, underneath the part/sleeve-shaped element 7 in the cartridge unit 4. This remains the case until the process of unfolding and positioning the heart valve prosthesis has reached the stage where its functionality can be checked.

If the check reveals incorrect functioning or faulty positioning, the part/sleeve-shaped element 7 can be pushed proximally again by one of the two operating elements 2 or 3 so that the anchoring support 10 with the heart valve prosthesis is at east partially accommodated in the cartridge unit 4 again and then the entire catheter can be removed from the patient by pulling it out of the aorta without causing damage to the vessel wall.

Figure 4:
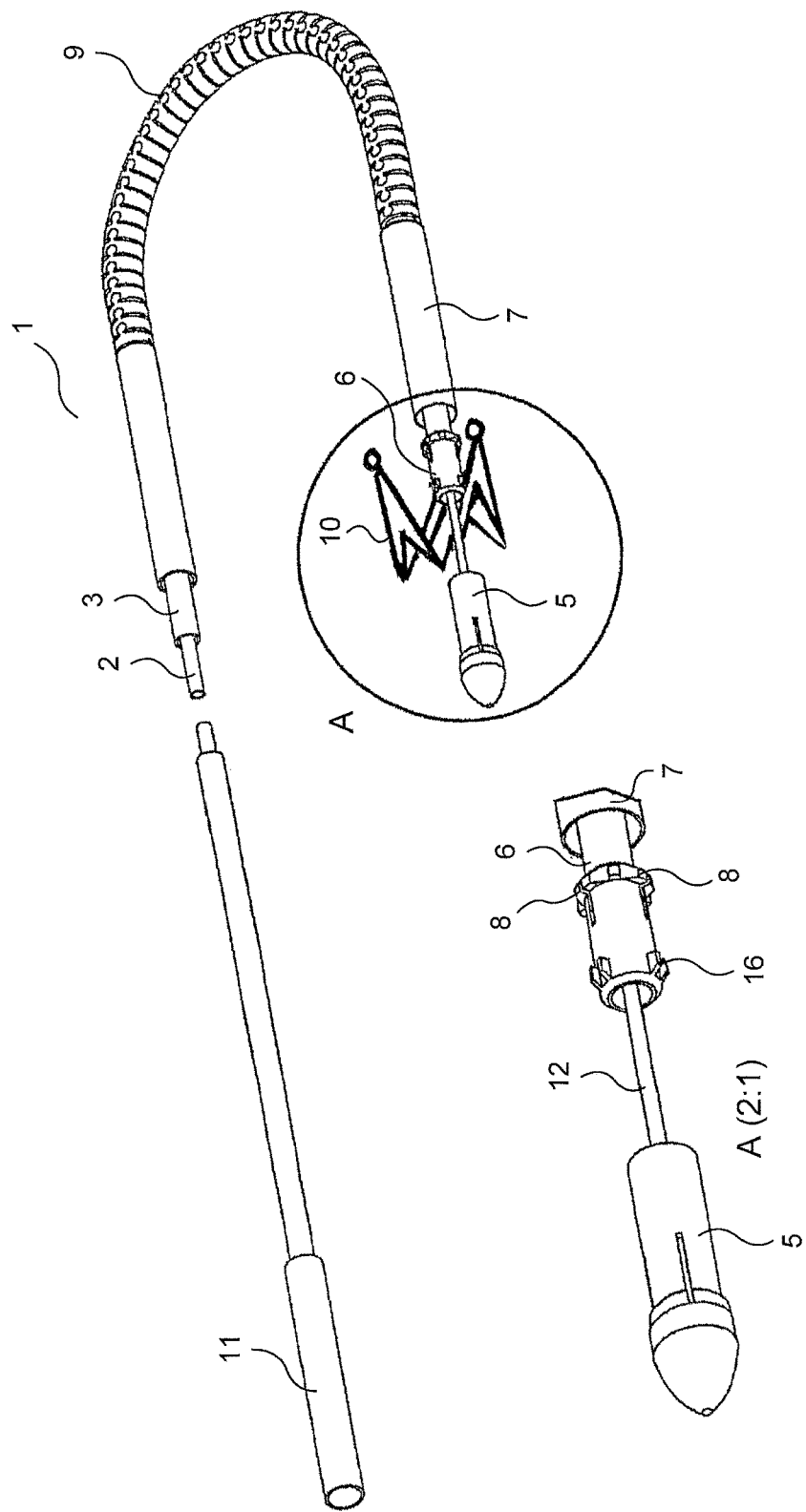

If the function test reveals that the heart valve prosthesis is able to fulfil its function to at least a sufficient capacity, the part/sleeve-shaped element 7 may be moved distally back, as illustrated in FIG. 4, or another part/sleeve-shaped element 6 of the cartridge unit 4 may be pushed in the proximal direction so that the distal part of the anchoring support 10 can also be released and expand fully.

As also illustrated in FIG. 4, eyes or other appropriate elements are provided at distal end regions of the anchoring support 10, which were previously engaged in anchoring elements 8 provided on the part/sleeve-shaped element 6. These eyes and the anchoring elements 8 ensure reliable retraction or extraction if it is established that an anchoring support 10 incorporating a heart valve prosthesis has been incorrectly or badly implanted, enabling the anchoring support 10 and heart valve prosthesis to be removed from the patient's body.

By means of the anchoring elements 8 as well as other guide elements 16 which may optionally be provided on the part/sleeve-shaped element 6 of the cartridge unit 4, it is also possible to effect a radial turning movement to enable the hoops of an anchoring support 10 to be introduced into the pockets of an old heart valve prosthesis in an exactly correct angular position, for example, in which case the entire catheter can be turned slightly about its longitudinal axis by the surgeon during the implantation.

Detail A of FIG. 4 also specifically illustrates a cannula 12, which is fed through the cartridge unit 4 along its longitudinal axis. By mans of the cannula 4, the guide wire described in the general part of the description can be fed through cartridge unit 4.

Figure 5:
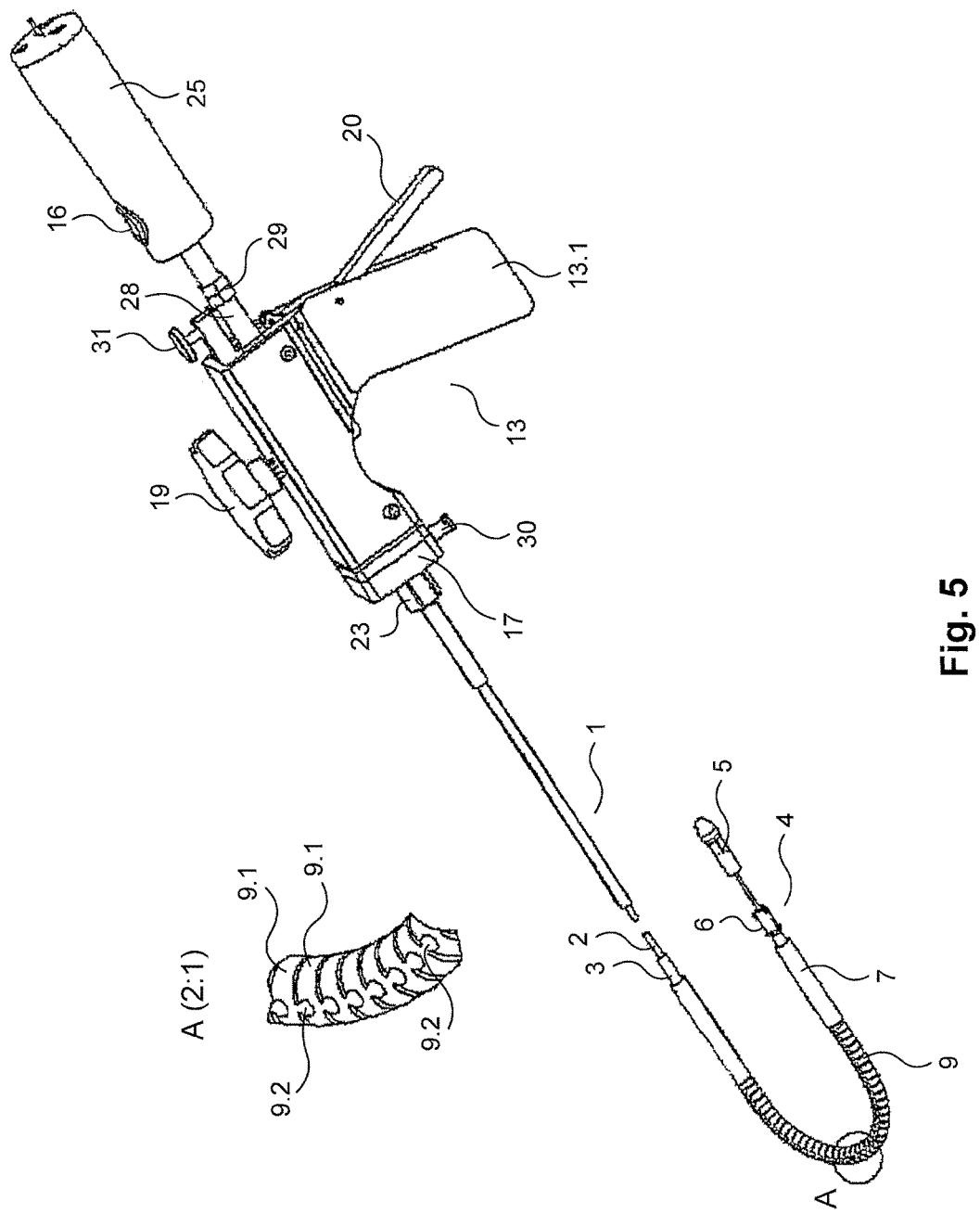
FIG. 5 shows an example of a catheter with a manipulating part.

FIG. 5 illustrates an example of a catheter with an additional manipulating part 13, on which other control elements are provided in order to permit manipulation.

The guide system 1 together with the cartridge unit 4 described above with reference to FIGS. 1 to 4 are also used in this example.

However, detail A illustrates one possible design of the bendable region 9 in the form of a link chain.

The individual links 9.1 are generally of the same shape and dimension.

In this respect, the oppositely lying end faces of the individual links 9.1 are shaped so as to form individual joints 9.2, each of which positively engages in adjacent individual links 9.1 and as a result of gaps with a sufficient gap width between the individual links 9.1 respectively ensure that the bendable region bends about at least 180° as mentioned above, with a radius of approximately 50 mm.

The individual joints 9.2 are formed by a cut-out in the respective oppositely lying end faces of the individual links 9.1, whereby a co-operating cut-out on one end face and a co-operating rounded, complementary protruding area on the diametrically opposite end face of the individual links 9.1 form the individual joints 9.2 on respective adjacent individual links 9.1.

Although not illustrated, the bendable region 9 may be enclosed by a plastic hose to render it fluid-tight.

FIG. 5 also illustrates how a manipulating part 13 may be provided to enable a catheter proposed by the invention to be introduced and manipulated.

A handle 13.1 is provided for introducing and extracting the catheter with the guide system 1 and cartridge unit 4.

A fluid-tight closure in the form of a plate 17 is provided in the proximal part of the manipulating part 13, enabling the guide system 1 to be flange-mounted by means of a locking nut 23, and seal elements are provided, although these are not illustrated here.

A standard Luer connection 30 is also provided, by means of which the coolant liquid can be circulated.

Figure 6:
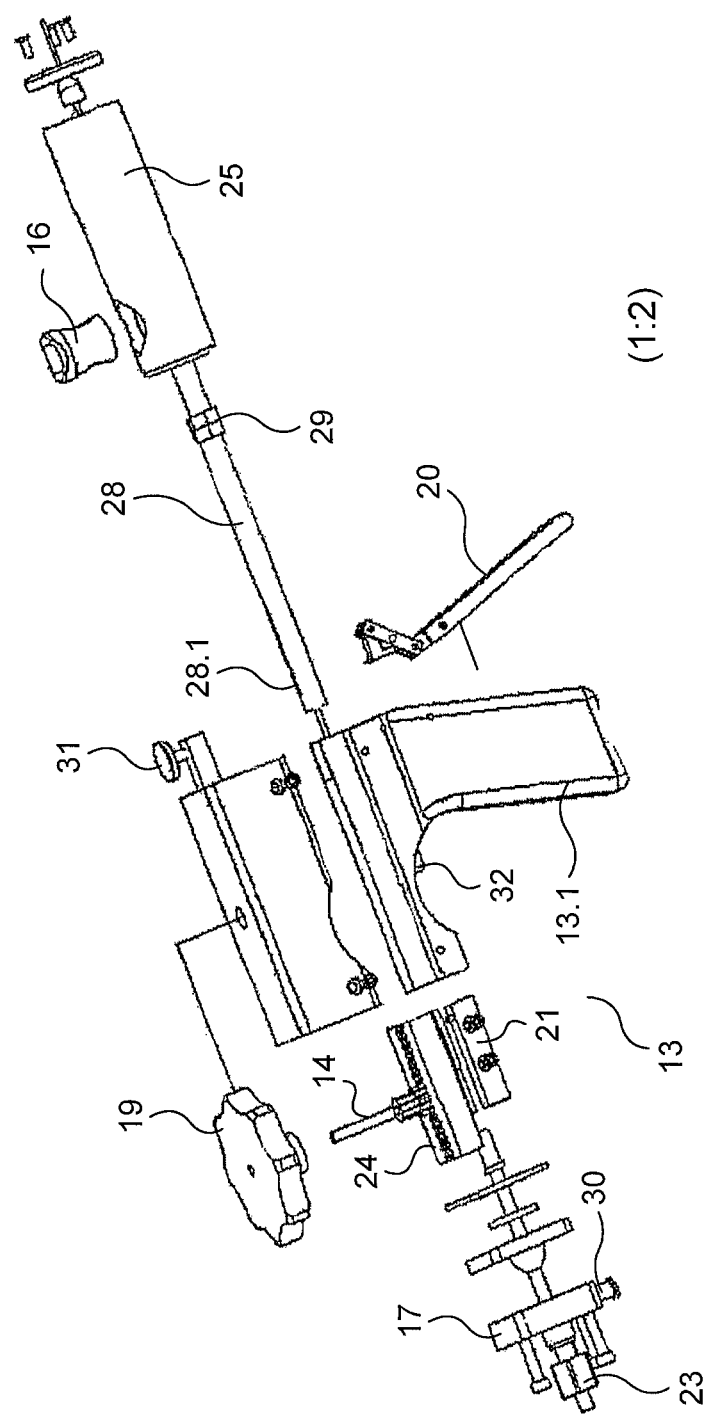
FIG. 6 is an exploded diagram illustrating the manipulating part illustrated in FIG. 5.

The respective curvature of the bendable region 9 can be obtained using the handle 19, which can be turned about an axis by means of tension cables (not illustrated) and this will be further explained with the description of FIG. 6.

The entire manipulating part 13 should be sealed with respect to the surrounding environment and with respect to the guide system 1 so that it is as far as possible fluid-tight and also gas-tight if necessary.

The tube 28 can be moved laterally in the proximal direction by means of the lever 20 acting on the handle 13.1, and the corresponding movement and resultant traction or compression force transmitted to one of the two operating elements 2 and/or 3, thereby enabling a manipulation of the individual parts/sleeve-shaped elements 5, 6 and/or 7 of the cartridge unit 4 in the manner described above, for example in finely measured doses via the pumping movements of the lever 20.

The pushing handle 25 enables the position of part 5 of the cartridge unit 4 to be manipulated relative to the sleeve-shaped part 6 of the cartridge unit 4 in the extension beyond the length of spring by means of the fixing hooks, serving as anchoring elements 8. The pushing handle 25 is latched in a thread-shaped toothing 28.1 of a tube 28 by means of a compression spring. As a result, the pushing handle 25 follows the proximal movement of the tube 28, which is connected to part 6 of the cartridge via the length of spring serving as an operating element 3.

On reaching an end stop marking the first discharge stage, the pushing handle 25 can be turned in order to effect a finely measured axial displacement of part 5 of the cartridge unit 4 relative to part 6 of the cartridge unit 4 in the direction of the pitch of the thread 28.1.

With respect to operating the pushing handle 25, the latter is able to move the part 5 of the cartridge unit 4 illustrated here without an additional fine adjustment.

Such a manipulation enables the anchoring support 10 to be released (see FIG. 3) and in this position, the anchoring support 10 can still be retracted.

When the stop 29 is released by means of an actuator member 31 provided in the form of an adjusting screw for example, the cartridge unit 4 may be extracted farther by operating the lever system 20 in the manner described above until the retaining eyes of the anchoring support 10 have moved away from the cartridge unit 4 and the anchoring support 10 is able to spring away from the anchoring elements 8 due to its expansion forces.

The elements of the cartridge unit 4 may be pulled back in stages. This being the case, part 5 of the cartridge unit 4 may be retracted by pulling back the pushing handle 25 (pushing element latched) beyond part 6 of the cartridge unit 4.

By operating a releasing bolt 32, part 6 of the cartridge unit 4 connected to the tube 28 can also be returned to its initial position by pulling the pushing handle 25 farther back so that the cartridge unit 4 is then completely closed again. In this state, the catheter can be removed from the patient's body again.

FIG. 6 is an exploded diagram providing a more detailed illustration of the manipulating part 13 used in this example.

As illustrated, when the handwheel 19 is turned via the shaft 14, two toothed racks 24 oriented parallel with one another can be displaced. Accordingly, one toothed rack 24 is moved in the proximal direction as the toothed rack 24 oriented parallel with it is moved in the distal direction.

Although these are not illustrated here, tension cables may be secured to clamping jaws 21 acting on the co-operating toothed racks 24, which are fed through the internally hollow guide system 1 as far as the bendable region 9 and are preferably secured in its proximal region.

By turning the handwheel 19 accordingly, a traction force can be applied to at least one of the two tension cables, causing the bendable region 9 to assume the appropriate curvature in measured doses so that the guide system 1 can be fed through the bend of the aorta in a defined manner together with the cartridge unit 4.

As also illustrated in FIG. 6, the lever 20 connected to the handle 13.1 acts via fine toothing 28.1 on the tube 28, enabling it to be manipulated via the operating elements 2 and/or 3 to permit the sequential release of the anchoring support 10.

The invention claimed is:

1. A catheter system comprising:
a prosthetic heart valve comprising a heart valve prosthesis attached to a support, wherein the support extends from a first end to a second end, and the second end of the support comprises retaining elements; and
a catheter for transvascular delivery of the prosthetic heart valve, the catheter comprising:
a guide system comprising a cartridge that includes a tip, an outer sleeve, and an inner sleeve, wherein the outer sleeve and the inner sleeve are configured to retain the prosthetic heart valve in a collapsed state radially therebetween, the inner sleeve including anchoring elements for engaging the retaining elements of the prosthetic heart valve, and wherein the outer sleeve and the inner sleeve are movable relative to each other along a longitudinal axis of the guide system for uncovering the prosthetic heart valve; and
a manipulating part coupled to the guide system for controlling movement of the guide system, the manipulating part comprising:
a handle;
a tube comprising outer threads;
a first actuator coupled to the handle, wherein a first movement of the manipulating part, including rotation of the first actuator relative to the handle, causes relative axial movement between the outer sleeve and the inner sleeve to uncover the prosthetic heart valve; and
a second actuator coupled to the handle, wherein a second movement of the manipulating part, including movement of the second actuator in a proximal-distal direction of the catheter, causes relative movement between the tip and the outer sleeve.

2. The system of claim 1, wherein rotation of the first actuator relative to the handle engages the threads of the tube to cause movement of the tube along a longitudinal axis of the tube.

3. The system of claim 1, wherein movement of the second actuator in the proximal-distal direction is independent of rotation of the first actuator.

4. The system of claim 1, wherein the manipulating part includes a stop to limit movement of the tube relative to the handle.

5. The system of claim 1, wherein the retaining elements of the support define holes for receiving the anchoring elements of the inner sleeve.

6. The system of claim 1, wherein the outer sleeve is configured to completely cover the inner sleeve and the prosthetic heart valve to retain the prosthetic heart valve in the collapsed state.

7. The system of claim 1, wherein the manipulating part is configured to retract the prosthetic heart valve within the outer sleeve when the first end of the support is uncovered and the second end is covered by the outer sleeve.

8. The system of claim 1, wherein the support is self-expanding.

9. The system of claim 1, wherein the heart valve prosthesis is attached to the support by stitching.

10. A catheter system comprising:
a prosthetic heart valve comprising a heart valve prosthesis attached to a self-expanding support, wherein the support extends from a first end to a second end, and the second end of the support comprises two retaining elements; and
a catheter for transvascular delivery of the prosthetic heart valve, the catheter comprising:
a guide system comprising a cartridge that includes a tip, an outer sleeve, and an inner sleeve, wherein the outer sleeve and the inner sleeve are configured to retain the prosthetic heart valve in a collapsed state radially therebetween, the inner sleeve including anchoring elements for engaging the retaining elements of the prosthetic heart valve, and wherein the outer sleeve and the inner sleeve are movable relative to each other along a longitudinal axis of the guide system for uncovering the prosthetic heart valve; and
a manipulating part coupled to the guide system for controlling movement of the guide system, the manipulating part comprising:
a handle;
a tube comprising outer threads;
a first actuator coupled to the handle, wherein a first movement of the manipulating part, including rotation of the first actuator relative to the handle to engage the threads of the tube, causes relative axial movement between the outer sleeve and the inner sleeve to uncover the prosthetic heart valve in a direction from the first end of the support to the second end of the support; and a second actuator coupled to the handle, wherein a second movement of the manipulating part, including movement of the second actuator in a proximal-distal direction of the catheter, causes relative movement between the tip and the outer sleeve, independent of rotation of the first actuator.

11. The system of claim 10, wherein the first actuator controls movement of the tube along a longitudinal axis of the tube.

12. The system of claim 10, wherein when the prosthetic heart valve is retained radially between the inner sleeve and the outer sleeve in the collapsed state, the first end of the support is adjacent to the tip.

13. The system of claim 10, wherein each retaining element of the support defines a hole for receiving a corresponding anchoring element of the inner sleeve in order to anchor the prosthetic heart valve to the catheter.

14. The system of claim 10, wherein the guide system comprises a bendable region configured to navigate a bend in an aorta during transvascular delivery of the prosthetic heart valve.

15. The system of claim 10, wherein the manipulating part comprises a fluid port in communication with the cartridge.

16. A catheter system comprising:

a prosthetic heart valve comprising a heart valve prosthesis stitched to a support, wherein the support extends from a first end to a second end, and the second end of the support comprises retaining elements; and a catheter for transvascular delivery of the prosthetic heart valve, the catheter comprising:

a guide system comprising a cartridge that includes a tip, an outer sleeve, and an inner sleeve, wherein the outer sleeve and the inner sleeve are configured to retain the prosthetic heart valve in a collapsed state radially therebetween, the inner sleeve including anchoring elements for engaging the retaining elements of the prosthetic heart valve, and wherein the outer sleeve and the inner sleeve are movable relative to each other along a longitudinal axis of the guide system for uncovering the prosthetic heart valve; and a manipulating part coupled to the guide system by a bendable region configured to navigate a bend in an aorta during delivery of the prosthetic heart valve, the manipulating part comprising:

a handle;

a tube comprising outer threads;

a first actuator coupled to the handle, wherein a first movement of the manipulating part, including rotation of the first actuator relative to the handle to engage the threads of the tube, causes relative axial movement between the outer sleeve and the inner sleeve to uncover the prosthetic heart valve in a direction from the first end of the support to the second end of the support; and a second actuator coupled to the handle, wherein a second movement of the manipulating part, including movement of the second actuator in a proximal-distal direction of the catheter, causes relative movement between the tip and the outer sleeve;

wherein the manipulating part is configured to retract the prosthetic heart valve within the outer sleeve when the first end of the support is uncovered and the second end is covered by the outer sleeve.

17. The system of claim 16, wherein the manipulating part further comprises:

a stop to limit movement of the tube relative to the handle; and a fluid port in communication with the cartridge.

18. The system of claim 16, wherein the support includes exactly two retaining elements, each retaining element defining a hole.

19. The system of claim 16, wherein the first actuator engages the threads by rotating about a longitudinal axis of the tube.

20. The system of claim 19, wherein rotation of the first actuator is independent of movement of the second actuator in the proximal-distal direction.

* * * * *